(12) United States Patent
Phan et al.

(10) Patent No.: US 9,815,868 B2
(45) Date of Patent: Nov. 14, 2017

(54) PEPTIDES BINDING TO PARALLEL-STRANDED G-QUADRUPLEXES

(71) Applicant: NANYANG TECHNOLOGICAL UNIVERSITY, Singapore (SG)

(72) Inventors: Anh Tuan Phan, Singapore (SG); Brahim Heddi, Singapore (SG); Vee Vee Cheong, Singapore (SG); Herry Martadinata, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days.

(21) Appl. No.: 14/892,087

(22) PCT Filed: May 20, 2014

(86) PCT No.: PCT/SG2014/000220
§ 371 (c)(1),
(2) Date: Nov. 18, 2015

(87) PCT Pub. No.: WO2014/189468
PCT Pub. Date: Nov. 27, 2014

(65) Prior Publication Data
US 2016/0115201 A1 Apr. 28, 2016

Related U.S. Application Data

(60) Provisional application No. 61/825,210, filed on May 20, 2013.

(51) Int. Cl.
| | |
|---|---|
| *A61K 38/00* | (2006.01) |
| *A61K 38/04* | (2006.01) |
| *A61K 38/10* | (2006.01) |
| *C07K 14/00* | (2006.01) |
| *C07K 7/08* | (2006.01) |
| *G01N 33/68* | (2006.01) |
| *C12Q 1/68* | (2006.01) |

(52) U.S. Cl.
CPC ............... *C07K 7/08* (2013.01); *C07K 14/00* (2013.01); *C12Q 1/6876* (2013.01); *G01N 33/68* (2013.01); *A61K 38/00* (2013.01); *C12Q 1/68* (2013.01)

(58) Field of Classification Search
CPC ........ A61K 38/00; A61K 38/04; A61K 38/10; C07K 14/00; C07K 7/08; G01N 33/68

USPC .......................................... 514/21.4; 530/326
See application file for complete search history.

(56) References Cited

U.S. PATENT DOCUMENTS

2005/0196754 A1* 9/2005 Drmanac ............ C07K 14/8107
435/6.11

FOREIGN PATENT DOCUMENTS

WO 01/75067 A2 10/2001

OTHER PUBLICATIONS

Booy et al., "The RNA helicase RHAU (DHX36) unwinds a G4-quadruplex in human telomerase RNA and promotes the formation of the P1 helix template boundary," *Nucleic Acids Research* 40(9):4110-4124 (2012).
Chalupnikova et al., "Recruitment of the RNA Helicase RHAU to Stress Granules via a Unique RNA-binding Domain," *The Journal of Biological Chemistry* 283(50):35186-35198 (Dec. 12, 2008).
Creacy et al., "G4 Resolvase 1 Binds Both DNA and RNA Tetramolecular Quadruplex with High Affinity and is the Major Source of Tetramolecular Quadruplex G4-DNA and G4-RNA Resolving Activity in HeLa Cell Lysates," *The Journal of Biological Chemistry* 283(50):34626-34634 (Dec. 12, 2008).
Tran et al., "Facilitation of mRNA Deadenylation and Decay by the Exosome-Bound, DExH Protein RHAU," *Molecular Cell* 13:101-111 (Jan. 16, 2004).
Lattmann et al., "Role of the amino terminal RHAU-specific motif in the recognition and resolution of guanine quadruplex-RNA by the DEAH-box RNA helicase RHAU," *Nucleic Acids Research* 38(18):6219-6233, 2010.
Sexton et al., "The 5' Guanosine Tracts of Human Telomerase RNA Are Recognized by the G-Quadruplex Binding Domain of the RNA Helicase DHX36 and Function to Increase RNA Accumulation," *Molecular and Cellular Biology* 31(4):736-743, 2011.
Sissi et al., "The Evolving world of protein-G-quadruplex recognition: A medicinal chemist's perspective," *Biochimie* 93:1219-1230, 2011.

* cited by examiner

*Primary Examiner* — Julie Ha
(74) *Attorney, Agent, or Firm* — Seed IP Law Group LLP

(57) ABSTRACT

A peptide comprising or consisting of the amino acid sequence of SEQ ID NO:1 or a derivative thereof is provided. Also provided are conjugates of such a peptide, the use of the peptide or the conjugates as a medicament, and methods for the detection of parallel-stranded G-quadruplexes.

5 Claims, 14 Drawing Sheets

Figure 1

| SEQ ID NO: | Name | Sequences (5'-3') | Structure[a] | Binding[b] |
|---|---|---|---|---|
| RNA | | | | |
| 4 | TERC18 | GGGUUGCGGAGGGUGGGC | Parallel | + |
| 5 | 12-nt TER | UAGGGUUAGGGU | Parallel | + |
| 6 | 10-nt TER | GGGUUAGGGU | Parallel | + |
| DNA | | | | |
| 7 | T95_2T | TTGGGTGGGTGGGTGGGT | Parallel | + |
| 8 | Pu24T | TGA GGG TGG TGA GGG TGG GGA | Parallel | + |
| 9 | CEB1 | AGGGGGGAGGGAGGGTGG | Parallel | + |
| 10 | CEB25 | AAGGGTGGGTGTAAGTGTGGGTGGGT | Parallel | + |
| 11 | 93del | GGGGTGGGAGGAGGGT | Parallel | + |
| 12 | HT1 | TTGGGTTAGGGTTAGGGTTAGGGA | Non-Parallel | − |
| 13 | Htelo1 | TAGGGTTAGGGTTAGGGTTAGGG | Non-Parallel | − |
| 14 | Htelo2 | TAGGGTTAGGGTTAGGGTTAGGGTT | Non-Parallel | − |
| 15 | Htelo3 | GGGTTAGGGTTAGGGTTAGGGT | Non-Parallel | − |
| 16 | Htelo4 | AGGGCTAGGGCTAGGGCTAGGG | Non-Parallel | − |
| 17 | DX | CGCGAATTCGCG | Duplex | − |
| 18 | ST95 | ACCCACCCACCCACCCAAAGATCCGAA AGGATCUTTGGGTGGGTGGGTGGGT | Stem-loop | − |

[a] Structures formation were monitored by NMR
[b] A negative binding is considered when the dissociation constant (Kd) is larger than 10μM.

Figure 2

| SEQ ID NO: | Name | Sequences (N$_{term}$-C$_{term}$) | Binding[a] |
|---|---|---|---|
| 19 | Rhau55 | SMHPGHLKGREIGMWYAKKQGQKNKEAERQERAVVHMDERREEQTVQLLNSVQAK | + |
| 20 | Rhau29 | HPGHLKGREIGMWYAKKQGQKNKEAERQE | + |
| 21 | Rhau23 | HPGHLKGREIGMWYAKKQGQKNK | + |
| 22 | Rhau20 | HPGHLKGREIGMWYAKKQGQ | + |
| 23 | Rhau18 | HPGHLKGREIGMWYAKKQ | + |
| 24 | Rhau18sm | SMHPGHLKGREIGMWYAKKQ | + |
| 1 | Rhau16 | HPGHLKGREIGMWYAK | + |
| 25 | Rhau14 | HPGHLKGREIGMWY | - |
| 26 | Rhau12 | HPGHLKGREIGM | - |
| 27 | Rhau5 | HPGHL | - |
| 28 | Rhau9 | KGREIGMWY | - |
| 29 | Rhau15' | KGREIGMWYAKKQGQ | - |
| 30 | Rhau20m1 | HPLHLKLREIMWYAKKQGQ | - |
| 31 | Rhau20m2 | HPGHLKGREIGMAAAKKQGQ | - |

[a] A negative binding is considered when the dissociation constant (Kd) is larger than 10μm

PEPTIDES BINDING TO PARALLEL-STRANDED G-QUADRUPLEXES

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690148_498USPC_SEQUENCE_LISTING.txt. The text file is 16 KB, was created on Nov. 16, 2015, and is being submitted electronically via EFS-Web.

FIELD OF THE INVENTION

The present invention lies in the field of biochemistry and relates to a peptide comprising or consisting of the amino acid sequence of SEQ ID NO:1 or a derivative thereof. The present invention also relates to conjugates of said peptide, the use of the peptide or the conjugate as a medicament and to methods for the detection of parallel-stranded G-quadruplexes.

BACKGROUND OF THE INVENTION

G-quadruplexes are non-canonical nucleic acid structures, formed by the stacking of G-tetrads and stabilized by cations (Phan, A T (2010) FEBS Journal, 277, 1107). Guanine-rich sequences, found ubiquitously in the genome of various species including the human genome, are able to fold into G-quadruplexes. Interestingly, these sequences are non-randomly distributed; they are localized in specific parts of the genome including the telomeres and promoter regions (Todd, A. K et al. (2005) Nucleic Acids Res, 33, 2901; Huppert, J. L. and Balasubramanian, S. (2005) Nucleic Acids Res, 33, 2908; Huppert, J. L. (2008) Biochimie, 90, 1140).

For a long time, these structures were believed to have no relevant contribution to biological processes. However, during the past decade strong evidences were found and pointed to significant roles of G-quadruplex structures in biological processes. In fact, it has been now established that G-quadruplexes are involved in essential cellular functions such as transcription, replication and recombination (Piazza, A et al. (2010) NucleicAcidsRes, 38, 4337; Biffi, G et al. (2013) Nat Chem, 5, 182; Rodriguez, R et al. (2012) Nat ChemBiol, 8, 301). For example, the formation and stabilization of G-quadruplexes has been shown to promote genomic instability of mini-satellites in yeast cells (Piazza, A et al. (2010) Nucleic Acids Res, 38, 4337).

It has been shown that formation and stabilization of G-quadruplexes in telomeres regions, in the promoters of oncogenes, or in the 5'-UTR regions of pre-mRNA oncogenes has anti-cancer effects (Sun, D. et al. (1997) J Med Chem 40, 2113; Mergny J. L., Helene C. (1998) Nat Med. 4, 1366; Balasubramanian, S and Neidle, S (2009) CurrOpinChemBiol, 13, 345). These recent findings stimulated the development of synthetic compounds meant to induce/stabilize G-quadruplex structures. For example, Telomestatin (Shin-ya, K et al. (2001) J Am ChemSoc, 123, 1262) and Phen-DC3 (De Cian et al. (2007) J Am ChemSoc, 129, 1856) are among the most relevant compounds, which bind to G-quadruplexes with a high affinity (with a dissociation constant $K_d$ in the nanomolar range) and a good selectivity against duplex and single-stranded nucleic acids.

G-quadruplex structures are highly diverse in regard of relative strand orientations and loop types, resulting in different topologies including a (i) parallel-type in which four strands point in the same direction; an (ii) hybrid "3+1" type in which three strands point in one direction and the fourth strand points in the opposite one; (iii) an antiparallel-type in which two strands point in one direction and two strands point in the opposite direction. Those topologies lead to different structural molecular shapes, with various loops and grooves of different size and accessibility (Phan, A T (2010) FEBS Journal, 277, 1107). The structural polymorphism of G-quadruplexes depends on their nucleotide sequences and the environmental conditions. In the human genome, G-rich sequences are scattered in different regions of the chromosomes and can form different possible G-quadruplex topologies. So far, most of G-quadruplex binders do not present selectivity against different G-quadruplex topologies and thus exhibit a wide-range genome effects (Biffi, G. et al. (2013) Nat Chem, 5, 182; Rodriguez, R et al. (2012) Nat ChemBiol, 8, 301).

Recently several proteins have been reported to interact with G-quadruplexes (Fry, M (2007) Front Biosci, 133, 9824; Murat, P et al. (2013) CurrOpin Genet Dev. 31, 22). One of such proteins is Rhau (also named DHX36 or G4R1). Rhau is a human helicase of the DEAH-box family, present in all type of cells (Tran, H et al. (2004) Mol Cell, 13, 101) and associated with different functions, including the formation of stress granules, interchromatin granule clusters (Chalupnikova, K et al. (2008) J BiolChem, 283, 35186) and the degradation of urokinase plasmonigen activator mRNA. Interestingly, studies by Nagamine and colleagues (Creacy, S D et al. (2008) J BiolChem, 283, 34626; Booy, E P et al. (2012) Nucleic Acids Res, 40, 4110) demonstrated that Rhau protein specifically unwind and bind G-quadruplexes nucleic acids. The G-quadruplex binding domain was identified to be in the N-terminal region of the protein, ranging from residue 53 to 105 (termed Rhau55).

Due to the structural diversity of G-quadruplexes, it is an object of the present invention to identify binders that selectively discriminate between different G-quadruplex topologies.

SUMMARY OF THE INVENTION

It is an object of the present invention to meet the above need by providing a peptide comprising or consisting of (i) the amino acid sequence of SEQ ID NO:1 or (ii) an amino acid sequence having at least 80% sequence identity to the amino acid sequence of SEQ ID NO:1 over its entire length. Surprisingly, the inventors have found that such peptide selectively binds to parallel-stranded G-quadruplexes. Hence, said peptide can be used as a medicament. Further, the specific binding to parallel-stranded G-quadruplexes provides the basis for methods to detect such G-quadruplexes. In addition, the present invention relates to conjugates comprising the above peptide.

In a first aspect, the present invention is thus directed to a peptide comprising or consisting of (i) the amino acid sequence of SEQ ID NO:1 or (ii) an amino acid sequence having at least 80% sequence identity to the amino acid sequence of SEQ ID NO:1 over its entire length.

In various embodiments of the invention, said peptide is 16 to 50 amino acids in length. In preferred embodiments, said peptide is 18 to 50 amino acids in length.

In a further aspect, the present invention relates to a conjugate comprising the peptide described above wherein said peptide further comprises at least one functional moiety.

In various embodiments of the invention, said at least one functional moiety is conjugated to the N-terminus of said peptide. In various other embodiments, said at least one functional moiety is conjugated to the C-terminus of said peptide. In still further embodiments, said at least one functional moiety does not comprise the amino acid sequence set forth in SEQ ID NO:2 or a C-terminal fragment thereof or said at least one functional moiety does not comprise the amino acid sequence set forth in SEQ ID NO:3 or an N-terminal fragment thereof.

In various embodiments of the invention, the functional moiety is a tag or a pharmaceutically active compound.

In a further aspect, the present invention relates to a peptide or a conjugate as described above for use as a medicament.

In a third aspect, the present invention relates to a method for the detection of parallel-stranded G-quadruplexes in a sample wherein said method comprises: contacting the peptide or the conjugate as described above with a sample suspected to contain a parallel-stranded G-quadruplex and detecting the presence or absence of the parallel-stranded G-quadruplex in said sample.

In a still further aspect, the present invention relates to the use of a peptide or a conjugate as described for the detection of parallel-stranded G-quadruplexes.

BRIEF DESCRIPTION OF THE DRAWINGS

The invention will be better understood with reference to the detailed description when considered in conjunction with the non-limiting examples and the accompanying drawings.

FIG. 1 shows the nucleotides and their corresponding sequences (SEQ ID Nos. 4-18) used in the present application.

FIG. 2 shows the peptides and their corresponding sequences (SEQ ID Nos. 19-31) used in the present application.

DETAILED DESCRIPTION OF THE INVENTION

Figure 3:
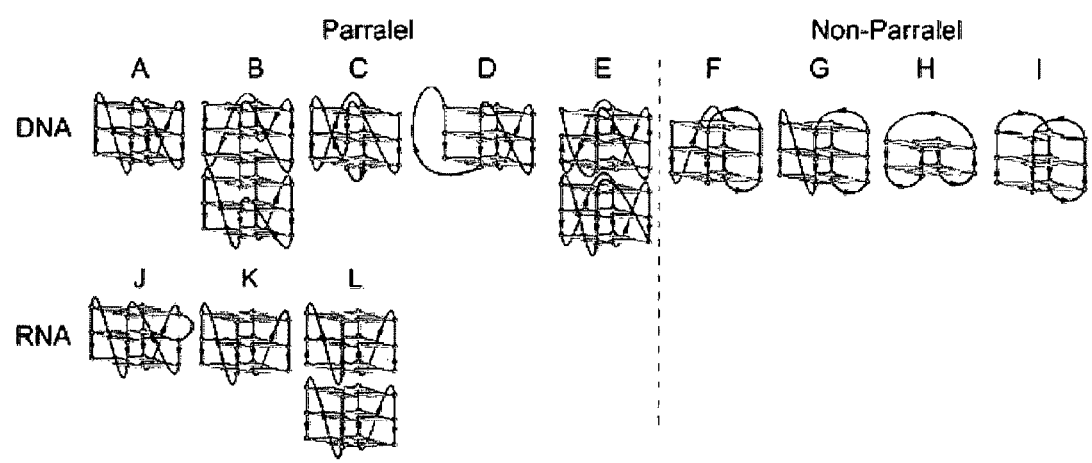
FIG. 3 (A) shows the folding topology of DNA and RNA G-quadruplexes used in this study. A) T95_2 T, B) 93del, C) Pu24t, D) CEB25, E) CEB1, F) Htelo1/HT1, G) Htelo2, H) Htelo3 I) Htelo4, J) TERC18, K) 12-nt TER and L) 10-nt TER. Guanines in anti and syn conformation are colored in gray and white respectively. Cytosines are colored in black.

The present inventors surprisingly found that a peptide comprising or consisting of (i) the amino acid sequence of SEQ ID NO:1 or (ii) an amino acid sequence having at least 80% sequence identity to the amino acid sequence of SEQ ID NO:1 over its entire length selectively binds to parallel-stranded G-quadruplexes.

Thus, in a first aspect, the present invention is thus directed to a peptide comprising or consisting of (i) the amino acid sequence of SEQ ID NO:1 or (ii) an amino acid sequence having at least 80% sequence identity to the amino acid sequence of SEQ ID NO:1 over its entire length.

In various embodiments of the invention, said peptide comprises or consists of an amino acid sequence having at least 85%, more preferably at least 90%, at least 95%, or at least 97% sequence identity to the amino acid sequence of SEQ ID NO:1 over its entire length.

In various embodiments of the invention, said peptide is 16 to 50 amino acids in length. In various other embodiments of the invention, said peptide is 16 to 1000, or more preferably 16 to 500, 16 to 200, 16 to 150, 16 to 100, 16 to 75, 16 to 40, 16 to 35, 16 to 30 or 16 to 25 amino acids in length, or said peptide is 18 to 1000, or more preferably 18 to 500, 18 to 200, 18 to 150, 18 to 100, 18 to 75, 18 to 50, 18 to 40, 18 to 35, 18 to 30 or 18 to 25 amino acids in length. In more preferred embodiments of the invention, the peptide of at least 18 amino acids in length comprises or consists of the peptide sequence set forth in SEQ ID NO:23.

In a further aspect, the present invention relates to a conjugate comprising the peptide described above wherein said peptide further comprises at least one functional moiety.

In various embodiments of the invention, said at least one functional moiety is conjugated to the N-terminus of said peptide. In various other embodiments, said at least one functional moiety is conjugated to the C-terminus of said peptide. In still various other embodiments, said at least one functional moiety is conjugated to the C-terminus and the N-terminus of said peptide. In further embodiments, said at least one functional moiety does not comprise the amino acid sequence set forth in SEQ ID NO:2 or a C-terminal fragment thereof or said at least one functional moiety does not comprise the amino acid sequence set forth in SEQ ID NO:3 or an N-terminal fragment thereof. In other various embodiments, if the functional moiety is a peptide and said peptide consists of at most 100, preferably 70, 50, 30, 25, 20, 15 or 10 amino acids.

In various embodiments of the invention, the functional moiety is a tag or a pharmaceutically active compound.

In a further aspect, the present invention relates to a peptide or a conjugate as described above for use as a medicament.

In another aspect, the present invention relates to a method for the detection of parallel-stranded G-quadruplexes in a sample wherein said method comprises: contacting the peptide or the conjugate as described above with a sample suspected to contain a parallel-stranded G-quadruplex and detecting the presence or absence of the parallel-stranded G-quadruplex in said sample.

In a still further aspect, the present invention relates to the use of a peptide or a conjugate as described for the detection of parallel-stranded G-quadruplexes.

The terms "polypeptide", "protein", and "peptide", which are used interchangeably herein, refers to a polymer of the 20 protein amino acids, or amino acid analogs, regardless of the size or function of the molecule. Although "protein" is often used in reference to relatively large polypeptides, and "peptide" is often used in reference to small polypeptides, usage of these terms in the art overlaps and varies. Thus, the above terms relate to one or more associated molecules, wherein the molecules consist of amino acids coupled by peptide (amide) bonds. The amino acids are preferably the 20 naturally occurring amino acids glycine, alanine, valine, leucine, isoleucine, phenylalanine, cysteine, methionine, proline, serine, threonine, glutamine, asparagine, aspartic acid, glutamic acid, histidine, lysine, arginine, tyrosine and tryptophan.

The peptides and conjugates of the invention can be synthesized synthetically or can be expressed in an organism or can be produced by in vitro transcription/translation. The peptides or conjugates may be expressed in, but such expression is not limited to *Escherichia Saccharomyces cerevisiae, Candida albicans, Pichia Pastoris,* insect cells such as Sf9 (*Spodoptera frugiperda*) cells, *Nicotiana* (tobacco plant) and CHO (Chinese hamster ovary) cells. Alternatively, the peptide or conjugate of the invention are expressed by an in vitro transcription/translationor "IVTT" system. "PITT reaction" or "in vitro transcription translation reaction", as interchangeably used herein, relates to cell-free systems that allow for specific transcription and translation by comprising macromolecular components (RNA polymerase, 70S or 80S ribosomes, tRNAs, aminoacyl-tRNAsynthetases, initiation, elongation and termination factors, etc.) required for transcription and translation. To ensure efficient translation, the system may also be supplemented with amino acids, energy sources (ATP, GTP), energy regenerating systems, and other co-factors ($Mg^{2+}$, $K^+$, etc.). Such systems or extracts are also known as "coupled" and "linked" systems as they start with DNA templates, which are subsequently transcribed into RNA and then translated. Preferred IVTT reactions comprise the rabbit reticulocyte lysate, the wheat germ extract and the *E. coli* cell-free system, in a more preferred embodiment the IVTT reaction is the rabbit reticulocyte lysate.

Preferably the synthesis of the peptide or conjugate of the invention is a synthetic synthesis. Methods of synthetic peptide synthesis include, but are not limited to liquid-phase peptide synthesis and solid-phase peptide synthesis (SPPS). Methods to produce peptides synthetically and according protocols are well-known in the art (Nilsson, B L et al. (2005) Annu Rev BiophysBiomolStruct, 34, 91). The synthesized peptides may be further modified by the attachment of additional chemical moieties.

The term "sequence", as used herein, relates to the primary nucleotide sequence of nucleic acid molecules or the primary amino acid sequence of a protein.

As used herein, "sequence identity" or "identity" in the context of two peptide sequences makes reference to the residues in the two sequences that are the same position when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.), BLAST (Jonhson, M et al. (2008) Nucleic Acids Research, 1, 36), Clustalw (EMBL-EBI), etc.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. The sequences may be aligned over their entire length or, optionally, only a specific region of one or both sequences may be used to generate the alignment.

The term "entire length", as used herein in the context of sequence identity, relates to the primary amino acid sequence of a given peptide ranging from the first amino acid at the N-terminus to the last amino acid at the C-terminus of said given peptide.

By the term "functional moiety", as used herein, any chemical molecule or group is meant that can be attached to the N-terminal or C-terminal end, or to any other residue of a peptide including protecting groups, fluorescent or otherwise detectable groups, tags, and/or pharmaceutically active compounds.

"Pharmaceutically active compound", as used herein, relates to a substance in a pharmaceutical drug or a pesticide that is biologically active. Such compounds encompass a broad chemical variety and relate to molecules of different classes according to Lipinski's rule of five such as small molecules, proteins, nucleotides, lipids, sugars, and derivatives thereof.

The term "medicament", as used herein, relates to any chemical substance formulated or compounded as single active ingredient or in combination with other pharmacologically active substances. The formulated or compounded composition may comprise, besides the pharmaceutically active compound, a pharmaceutically acceptable carrier.

"Tag", as used herein, relates to a group of atoms or a molecule that is attached covalently to a nucleic acid sequence or another biological molecule for the purpose of detection by an appropriate detection system. The term "tagged peptide" refers to a peptide to which a tag has been covalently attached. The term "tag" and "label" may be used interchangeably.

The term "N-terminus" relates to the start of a protein or polypeptide, terminated by an amino acid with a free amine group (—NH2).

The term "an N-terminal fragment" relates to a peptide or protein sequence which is in comparison to a reference peptide or protein sequence C-terminally truncated, such that a contiguous amino acid polymer starting from the N-terminus of the peptide or protein remains. In some embodiments, such fragments may have a length of at least 10, 20, 50, or 100 amino acids.

The term "C-terminus" relates to the end of an amino acid chain (protein or polypeptide), terminated by a free carboxyl group (—COOH).

The term "a C-terminal fragment" relates to a peptide or protein sequence which is in comparison to a reference peptide or protein sequence N-terminally truncated, such that a contiguous amino acid polymer starting from the C-terminus of the peptide or protein remains. In some embodiments, such fragments may have a length of at least 10, 20, 50, or 100 amino acids.

"At least one", as used herein, relates to one or more, in particular 1, 2, 3, 4, 5, 6, 7, 8, 9, 10 or more.

The term "G-quadruplex" refers to a four-stranded helical nucleic acid structure comprising multiple stacked G-tetrads, each of which consists of four guanine bases that associate in a cyclical manner through Hoogsteen hydrogen bonds and are further stabilized, through coordination to a cation in the center. The body of stacked G-tetrads, comprising a total of 2-8 layers, is collectively referred to as the G-tetrad core. Each of the four guanine columns constituting the G-tetrad core can arise from a single (continuous column), two, or four (discontinuous column) separate guanine stretch/es. The term "multimolecular" as used herein refers to a G-tetrad core that is formed by at least two separate oligonucleotide strands, each of which comprises at least one G-rich segment or partial G-rich segment. The term "parallel-stranded G-quadruplex", as used herein, relates to a G-quadruplex structure wherein all four strands point in the same direction. Such parallel-stranded G-quadruplex is formed, for example by the nucleotide sequence set forth in SEQ ID NO:5.

The term "conjugate," as used herein, refers to a compound comprising two or more molecules (e.g., peptides, carbohydrates, small molecules, or nucleic acid molecules) that are chemically linked. The two or molecules desirably are chemically linked using any suitable chemical bond (e.g., covalent bond). Suitable chemical bonds are well known in the art and include disulfide bonds, acid labile bonds, photolabile bonds, peptidase labile bonds (e.g. peptide bonds), thioether, and esterase labile bonds.

The term "detection", as used herein, relates to quantitatively or qualitatively identifying an analyte (e.g., DNA, RNA or a protein) within a sample. In preferred embodiments of the invention, the analyte is a parallel-stranded G-quadruplex. The absence or presence of the parallel-stranded G-quadruplex is determined by binding of the peptide or conjugate of the present invention to this G-quadruplex. The formed complex of the peptide or conjugate of the present invention and the parallel-stranded G-quadruplex can be detected by several different techniques known in the art. Such techniques may include, but are not limited to immunoassay, mass spectrometry, chromatography, Western Blot, or gel electrophoresis.

In some embodiments, the immunoassay may be, but is not limited to an Enzyme-linked Immunosorbent Assay (ELISA), Western blot, agglutination test, biotin/avidin type assays, radioimmunoassays, immunoelectrophoresis and immunoprecipitation. The reactions generally include revealing labels such as fluorescent, chemiluminescent, radioactive, enzymatic labels or dye molecules, or other methods for detecting the formation of a complex between the antigen and the antibody or antibodies reacted therewith. These and further immunoassays are well known in the art (David Wild (Ed.): The Immunoassay Handbook. 3rd ed. Elsevier Science Publishing Company, Amsterdam 2005).

More particularly, an ELISA method can be used, wherein the wells of a microtiter plate are coated with an antibody against the protein to be tested. A biological sample containing or suspected of containing the G-quadruplex and the peptide/conjugate of the invention are then added to the coated wells. After a period of incubation sufficient to allow the formation of antibody-antigen complexes, the plate(s) can be washed to remove unbound moieties and a detectably labelled secondary binding molecule added. The secondary binding molecule is allowed to react with any captured G-quadruplex-peptide/conjugate-complex, the plate washed and the presence of the secondary binding molecule detected using methods well known in the art.

In certain embodiments of the above detailed methods, if the determination is via mass spectrometry, the mass spectrometry may be selected from the group comprising MS measurements using EI, CI, ESI, APLI, APPI and APCI.

The analyte determination employing chromatography may be selected from the group comprising liquid chromatography, HPLC, FPLC, Smart chromatography, gel chromatography, size exclusion chromatography, reverse phase chromatography and ion-exchange chromatography (Introduction to Modern Liquid Chromatography, Lloyd R. Snyder, Wiley, 2009).

In various embodiments, if the analyte is detected via gel electrophoresis, the gel electrophoresis may be selected from the group, but not limited to agarose gel electrophoresis, sodium dodecyl sulfate poly acryl amide gel electrophoresis (SDS-PAGE), 2D-gel electrophoresis, native gel electrophoresis and quantitative preparative native continuous polyacrylamide gel electrophoresis (QPNC-PAGE).

Of course, in certain embodiments of the methods of the present invention at least two determination methods may be coupled to each other in a subsequent manner. In a variant, a gel electrophoresis may be followed by a mass spectroscopic analysis. Alternatively, a gel electrophoresis may be followed by a Western Blot, a chromatography may be followed by a mass spectroscopic analysis, and a chromatography may be followed by an immune assay, e.g. an ELISA.

Where in the methods detailed above an analyte is determined with the use of DNA labels, the DNA label may be determined by PCR, gel electrophoresis and/or Southern Blot.

The term "contacting", as used herein, refers generally to providing access of one component, reagent, analyte or sample to another. For example, contacting can involve mixing a solution comprising the peptide or conjugate of the invention with a sample comprising a G-quadruplex. The solution comprising one component, reagent, analyte or sample may also comprise another component or reagent, which facilitates mixing, interaction, uptake, or other physical or chemical phenomenon advantageous to the contact between components, reagents, analytes and/or samples.

In various embodiments of the invention, the sample is a biological sample, for example a body fluid, cell or tissue sample. Body fluids comprise, but are not limited to blood, blood plasma, blood serum, breast milk, cerebrospinal fluid, cerumen (earwax), endolymph and perilymph, gastric juice, mucus (including nasal drainage and phlegm), peritoneal fluid, pleural fluid, saliva, sebum (skin oil), semen, sweat, tears, vaginal secretion, nipple aspirate fluid, vomit and urine. The cell or tissue sample may comprise material originated from any part of the body such as connective tissue, muscle tissue, nervous tissue, and epithelial tissue. The term "obtaining a sample", as used herein, relates to different methods known in the art that comprise, but not limited to, biopsy, sentinel node biopsy or removal of blood, bone marrow, sputum or bronchial fluids.

EXAMPLES

Example 1: Rhau55 Binds Preferentially to Parallel G-Quadruplexes

Rhau55 was expressed in *Escherichia coli*. The binding of Rhau55 to different G-quadruplexes nucleic acids topology was first tested using gel electrophoresis.

Figure 6:
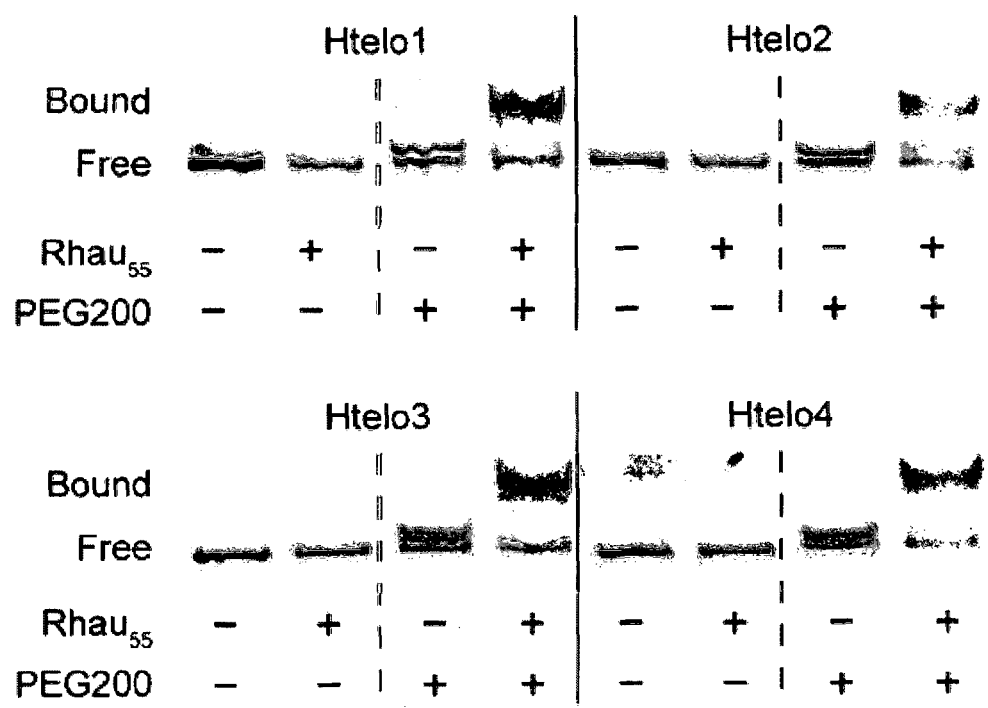
FIG. 6 shows the native gel electrophoresis of Htelo1, Htelo2, Htelo3, and Htelo4 in dilute and crowding condition (induced by 40% PEG (v/v)). DNA concentrations were fixed at 100 nM and Rhau55 was 1 µM, in 70 mM KCL and 20 mM phosphate buffer (pH=6.8). DNA on the gel was revealed using FAM or TAMRA fluorescence dye attached to the extremity of the DNA.
Figure 7:
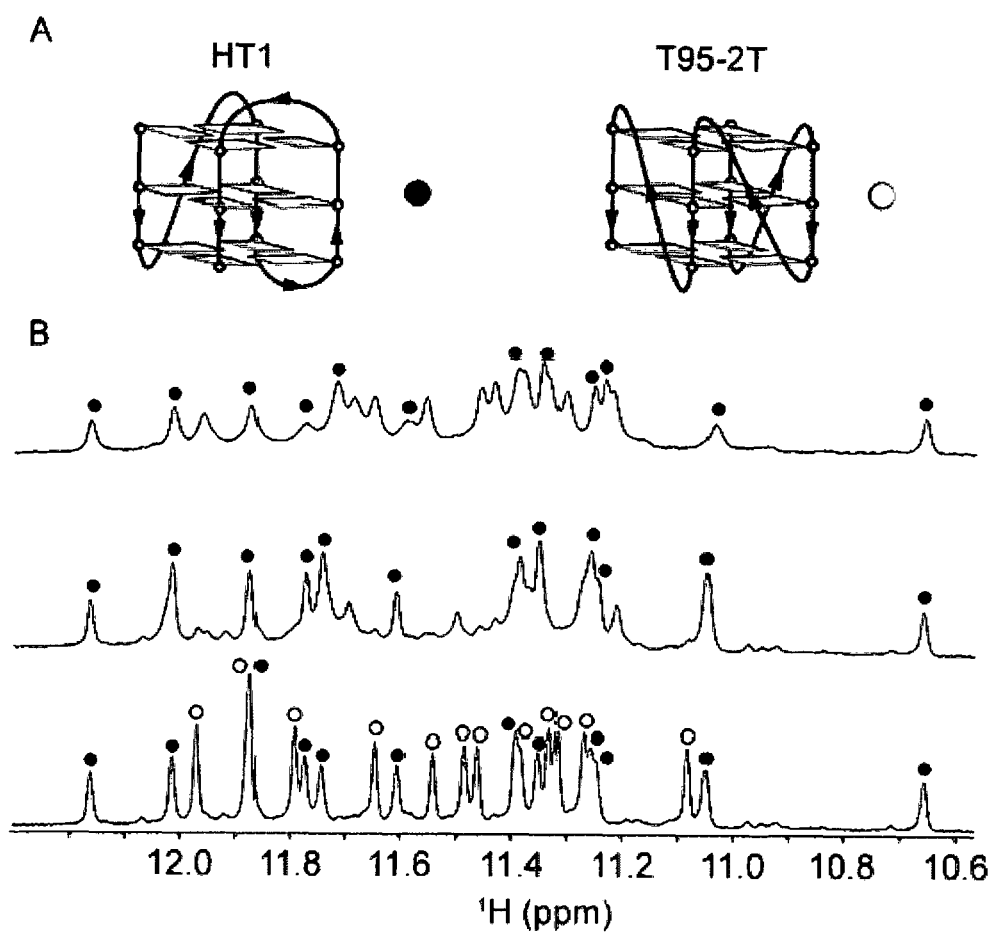
FIG. 7 shows the NMR imino proton spectra of a mixture of HT1 (filled dot) and T95_2 T (open dot), in the absence and the presence of different amount of Rhau55.
Figure 8:
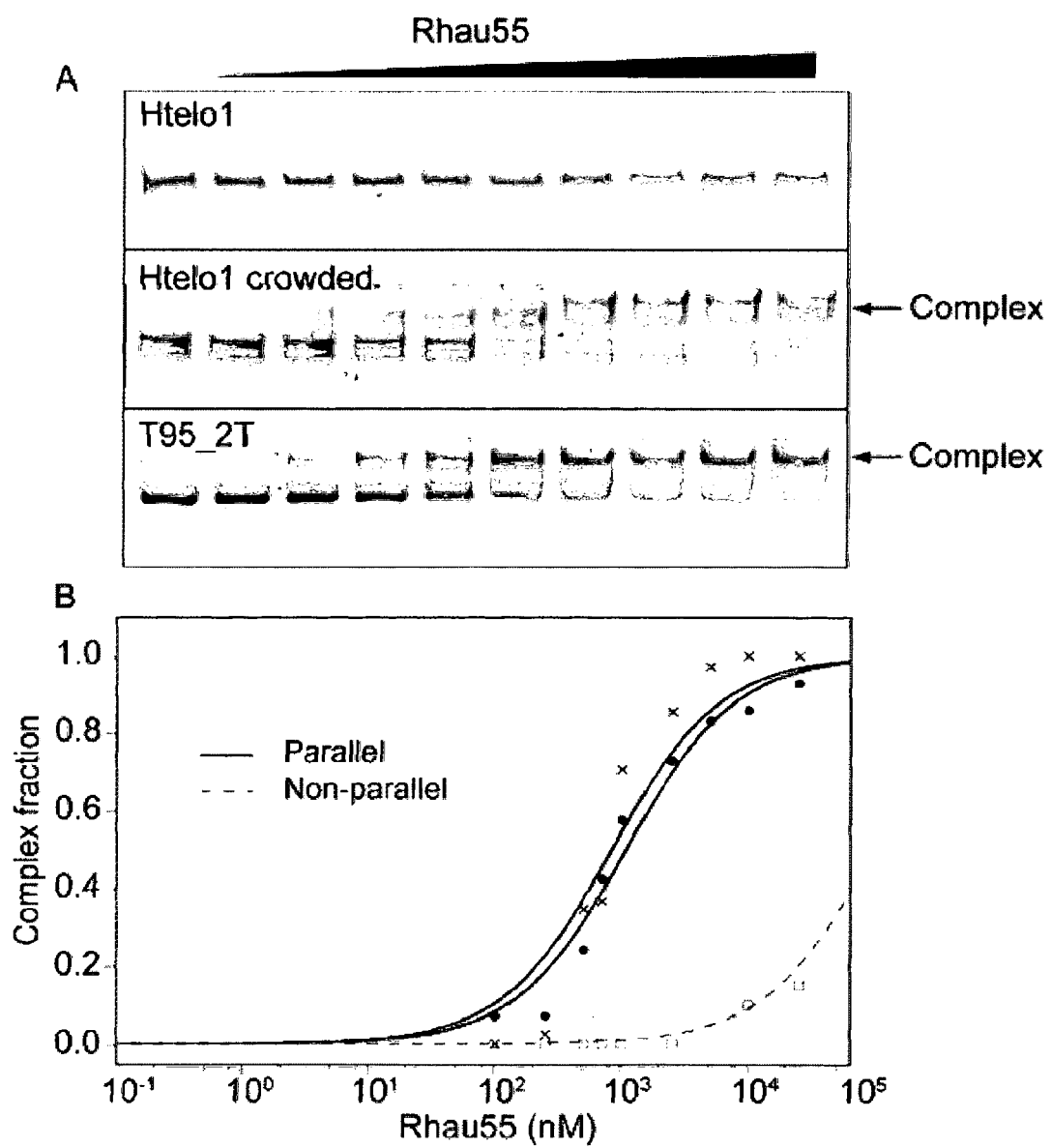
FIG. 8 shows the gel mobility shift assay for T95_2T, Htelo1 in dilute and crowding condition (induced by 40% PEG (v/v)) binding by Rhau55. (A) T95_2 T and Htelo1 at a concentration of 100 nM were incubated for 15 minutes at room temperature with an increasing concentration of Rhau55. (B) Quantification of gel electrophoresis assays bands of T95_2 T (black dot) and Htelo1 in dilute (open square) and crowding condition (black cross).

Rhau55 binds to various parallel G-quadruplexes DNA and RNA (FIGS. 1 and 3-5) but not to various forms of non-parallel G-quadruplexes (FIGS. 1 and 6). This result was confirmed by NMR spectroscopy (FIG. 7): adding Rhau55 in a mixture containing two well-defined intramolecular G-quadruplexes (a propeller parallel form (termed T95_2 T) and a non-parallel 1 (termed HT1) only affect the peaks of the former form.

To confirm that the observed selective effect was based on the structure rather than sequence, the binding of Rhau55 was tested using the human telomeric sequences in $K^+$-containing solution, with and without crowded condition (40% v/v PEG200). In diluted solutions the human telomeric sequences Htelo1, Htelo2, Htelo3 and Helo4 form a distinct and non-parallel G-quadruplex (Luu K N et al. (2006) J Am ChemSoc, 128(30), 9963-9970; Phan A T et al. (2006) Nucleic Acids Res, 34(19), 5715-5719; Lim K W et al. (2009) J Am ChemSoc, 131(12), 4301-430; Lim K W et al. (2009) Nucleic Acids Res, 37(18), 6239-6248), however in crowded conditions those sequences form a propeller-type parallel stranded G-quadruplex. The gel shift assay (FIG. 6) showed that Rhau55 binds significantly only to a parallel-type G-quadruplex.

Figure 4:
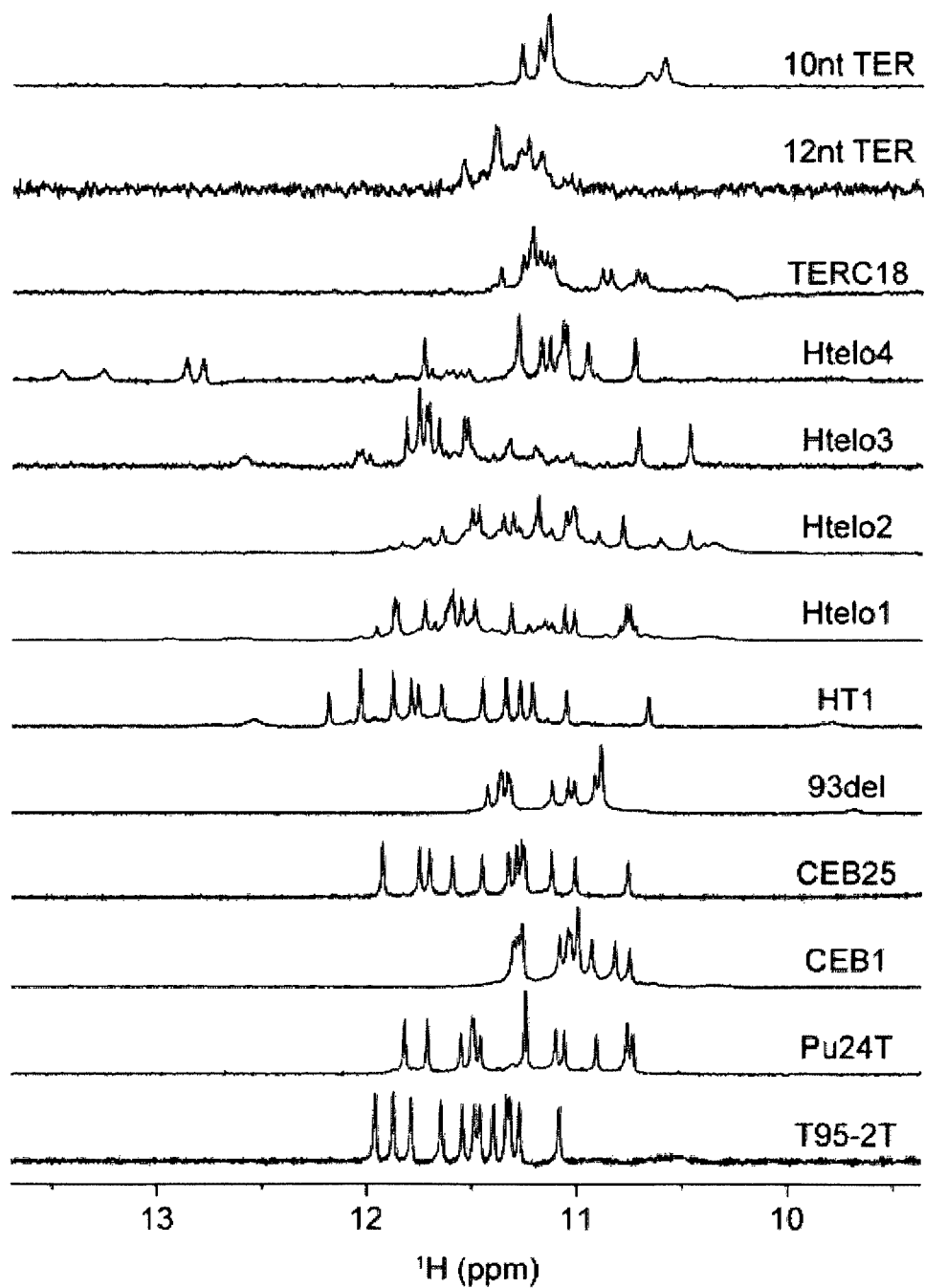
FIG. 4 shows the NMR imino protons of DNA and RNA G-quadruplexes sequences used in this study, name of the sequences are labeled on top of each spectrum.
Figure 5:
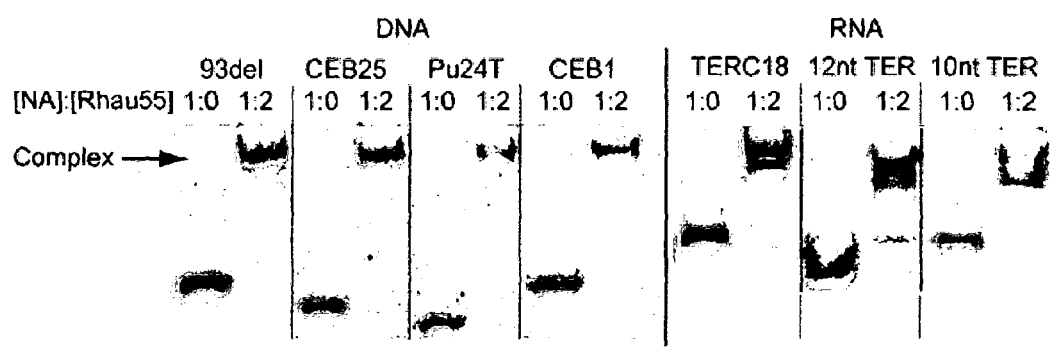
FIG. 5 shows the native gel electrophoresis of 93del, CEB25, Pu24T, CEB1, TERC18, 12 nt TER and 10 nt TER. The ratio between Rhau55 and Nucleic acids is indicated on top of each lane. DNA concentrations were fixed at 100 µM, in 70 mM KCL and 20 mM phosphate buffer (pH=6.8). DNA on the gel was revealed using UV shadowing.

Subsequently, a quantitative analysis of the interaction between Rhau55 and three G-quadruplexes was performed using gel electrophoresis (FIG. 4). The analysis indicated a dissociation constant of 1029 nM and 989 nM for the parallel-type form of Htelo1 (under crowded condition) and the single, loop propeller-type T95_2 T, respectively, consistent with previous published data for the full-length protein (Tran H et al. (2004) Mol Cell, 13, 101). In contrast an apparent binding of >10 µM was found with the hybrid "3+1" form 1, and an estimated Kd over 10 µM was found for Htelo2, Htelo3 and Hetol4 non-parallel forming sequences, highlighting a net preference for the human telomeric sequences forming a parallel-type G-quadruplex. From the data little effect on three (Htelo1, parallel form) and single (T95_2T) loop size was observed on Rhau55 binding affinity.

Example 2: NMR Analysis Reveals a Minimal Binding Domain

Figure 12:
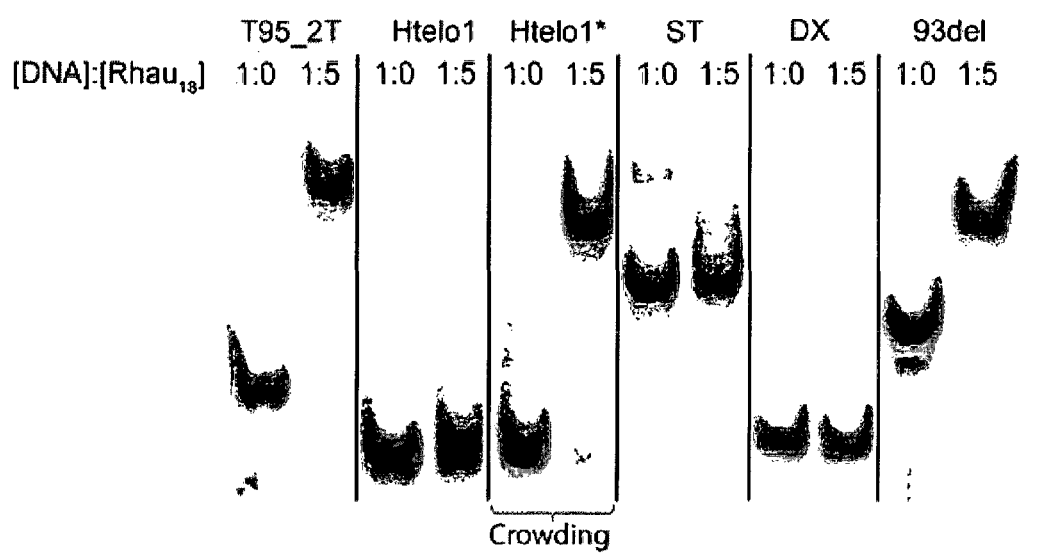
FIG. 12 shows the native gel electrophoresis of T95_2 T, Htelo1, Htelo1 in crowding condition (induced by 40% PEG (v/v)), ST, DX and 93del. The ratio between Rhau18 and DNA is indicated on top of each lane. DNA concentrations were fixed at 100 µM, in 70 mM KCL and 20 mM phosphate buffer (pH=6.8). DNA on the gel was revealed using UV shadowing.

The interaction between T95_2 T and Rhau55 was investigated. Backbone assignment of double labeled $^{15}N$, $^{13}C$ Rhau55 free and in complex were recorded using a series of classical triple resonances experiments. 93% of backbone $^{15}N$, $^{1}HN$, $^{1}H\alpha$, $^{13}C\alpha$, and $^{13}C'$ assignments have been performed for both free and bound Rhau55. Analysis of chemical shift by Talos+ (Shen Y et al. (2009) J. Biomol. NMR, 44, 213-223) and CD spectrum (data not shown) showed a predominant helical structure for the free Rhau55. The bound form of Rhau55 was obtained with an equimolar ratio of Rhau55 and T95_2 T (FIG. 12A).

Figure 9:
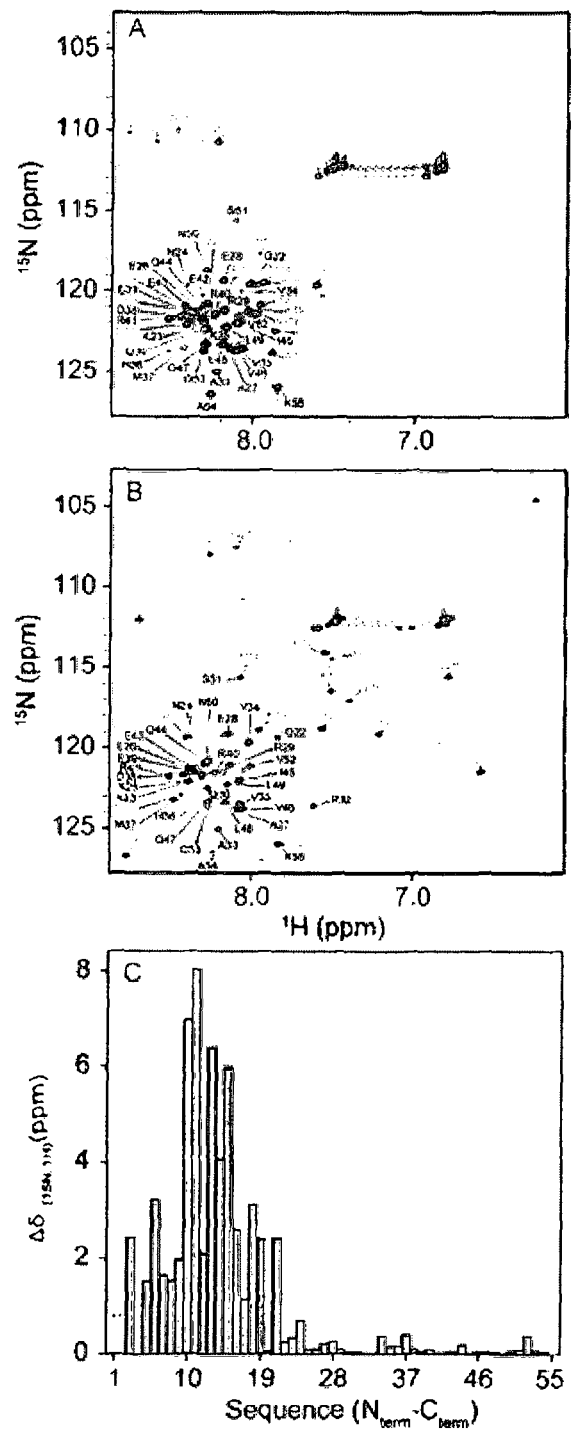
FIG. 9 shows the 2D $^1$H-$^{15}$N HSQC spectra of free Rhau55 (A) and bound to T95_2 T (B). (C) Chemical-shift variations $\Delta\delta$ (ppm)=$[(\Delta^{15}N)^2+(\Delta^1H)^2]^{1/2}$ between the free and bound Rhau55.

$^{1}H$, $^{15}N$-HSQC spectra of the free and bound Rhau55 are presented in FIGS. 9A and 9B, respectively. Chemical shift variation between the free and bound Rhau55 is shown in FIG. 9C. Significant chemical shift perturbations are present only in the first 20 amino acids, and no significant changes are observed for the rest of the sequence, which strongly suggests that the DNA binding occurs in that region.

Figure 10:
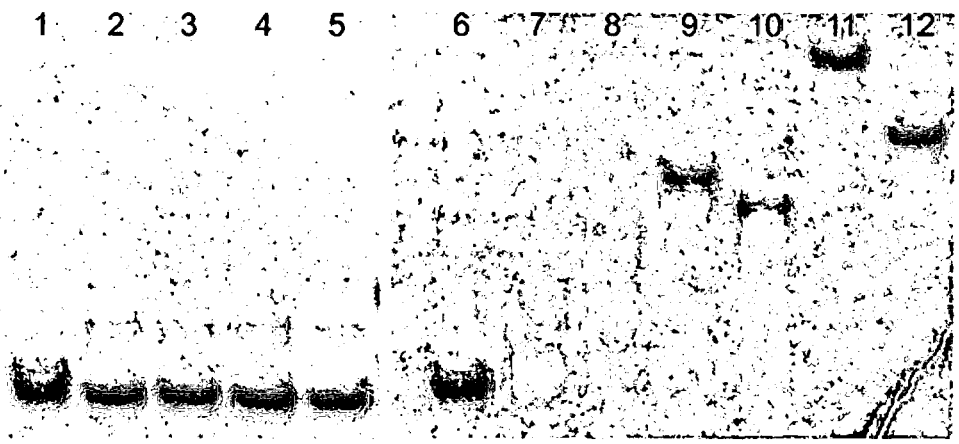
FIG. 10 shows the native gel electrophoresis of T95_2 T. Lane 1 T95_2 T, lane 2 to lane 12: addition of Rhau20m1, Rhau20m2, Rhau5, Rhau9, Rhau12, Rhau14, Rhau15 Rhau16, Rhau20, Rhau18, Rhau29 and Rhau23. DNA concentrations were fixed at 100 µM, in 70 mM KCL and 20 mM phosphate buffer (pH=6.8), and the ratio between peptide and DNA was kept at 1:5. DNA on the gel was revealed using UV shadowing.

Inferring from the NMR chemical shift variation data, several combinations of synthetic peptides containing the N-terminal region of Rhau55 ranging from 5 to 29 amino acids (according to the numbering of the sequence of Rhau55) were tested with T95_2T using gel electrophoresis (FIG. 10). These data show that the 16-amino-acid peptide Rhau16 constitutes the minimal domain required for the G-quadruplex binding. It should be noted that this domain contains a highly conserved 13-amino-acid sequence (PGHLKGREIGMWY) (SEQ ID NO: 32) that was previously identified as a major determinant for the G-quadruplex binding (Lattmann, S. Nucleic Acids Res 2010, 38, 6219). However, this 13-amino-acid sequence is not sufficient for G-quadruplex binding, as the Rhau14 peptide containing this sequence does not bind G-quadruplexes (FIG. 10, lane 6).

Figure 11:
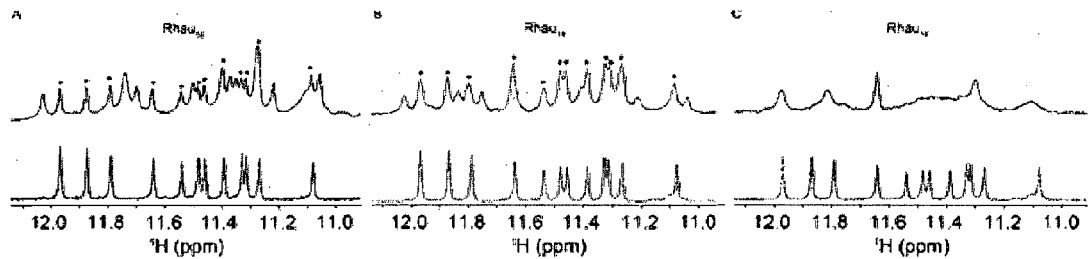
FIG. 11 shows the NMR imino proton spectra of T95_2 T titrated with increasing concentrations of Rhau55 (A), Rhau18 (B) and Rhau16 (C).

NMR imino proton spectra of T95_2 T in complex with Rhau16, Rhau18sm and Rhau55 using equimolar ratio is presented in FIG. 11. The NMR spectra of the complexes T95_2T-Rhau55 and T95_2T-Rhau18sm were very similar and occurred in the slow exchange regime, suggesting a similar binding mode, while the NMR spectrum of T95_2 T-Rhau16 is different from that of Rhau55 and occurred in a different NMR time scale regime. Thus, the further analysis was drawn to the binding of Rhau18sm with G-quadruplex.

A similar binding assay was performed with Rhau55. Gel electrophoresis assay of Rhau18sm was performed with a parallel single propeller loop T95_2 T, the hybrid "3+1" Htelo1, the parallel stranded G-quadruplex form of Htelo1 obtained under crowded condition, an interlocked dimeric parallel stranded G-quadruplex (termed 93del), the Dickerson B-DNA duplex (DX) and an stem-loop structure (ST).

The results showed (FIG. 12) that Rhau18m binds to parallel-type stranded G-quadruplex (monomeric and dimeric) but not with the hybrid "3+1", the duplex DNA or the stem-loop structure form. Rhau18sm behave similarly to that of Rhau55. Rhau18sm binds preferentially to parallel stranded G-quadruplex, with an affinity three order of magnitude. Then the interaction of Rhau18sm with T95_2 T was studied using NMR.

Figure 13:
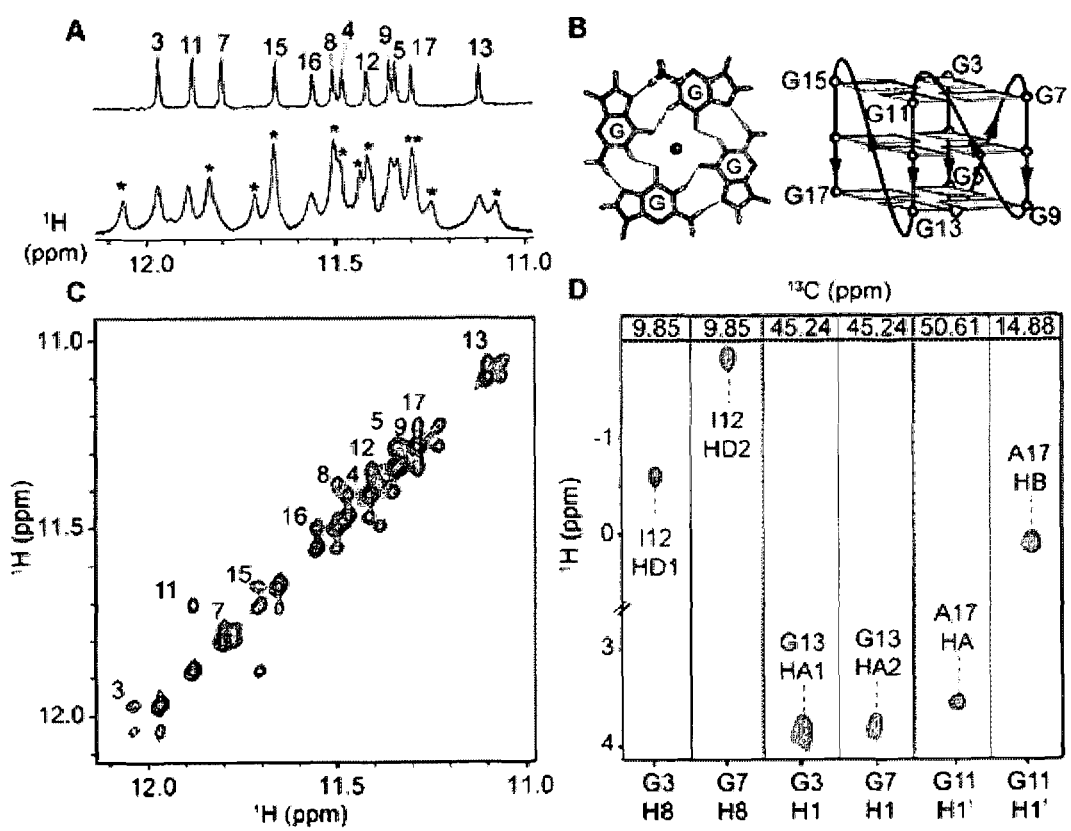
FIG. 13 shows the NMR imino proton spectra of T95_2 T (A) with increasing concentrations of Rhau18sm. Peaks arising from the complex are marked with asterix. Complex was obtained with an equimolar ratio of DNA and peptide. (B) G-tetrad representation and folding topology adopted by the T95_2 T sequence. (C) NOESY spectrum (mixing time 300 ms) at 370 C, exchange cross peak are labeled with residue number. (D) Strip plot showing the intermolecular cross peak from $^{13}$C-$^1$H HSQC-NOESY spectrum.
Figure 14:
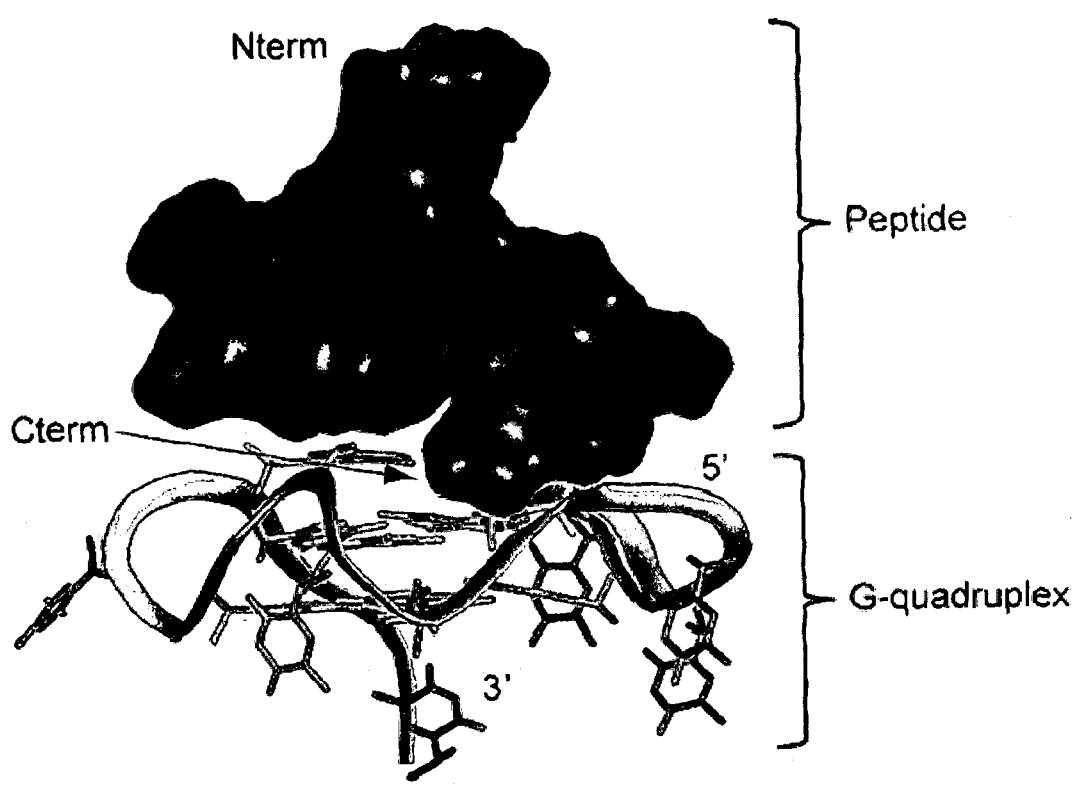
FIG. 14 shows the representation of an NMR-based model of the Rhau18-T95_2T complex. Rhau18 is colored in black and T95_2 T in white. Rhau18 is presented in surface mode and DNA in sticks mode.

Example 3: Structural Basis for the Discrimination of Parallel G-Quadruplexes by Rhau The complex formed by Rhau18sm and T95_2T, using fully $^{15}$N and $^{13}$C labeled protein and unlabeled DNA showed the presence of 12 imino protons in the bound form which indicated the persistence of three-layered G-quadruplex structure upon protein binding (FIG. 13A). Imino protons of T95_2 T in the complex were assigned through chemical exchange between the free and bound state (FIG. 13C). A parallel topology for the bound T95_2T was found using the NOE imino-aromatics cross-peaks of guanines (data not shown and FIG. 13B). Intramolecular NOE cross-peaks for the bound form of Rhau18sm were assigned manually with 3D $^{15}$N and $^{13}$C NOESY-HSQC and by comparing spectra from Rhau18sm in the free form. Using 2D 1H NOESY, 3D $^{15}$N, $^{13}$C HSQC-NOESY and 2D, 3D $^{15}$N, $^{13}$C-edited NOESY 42 intermolecular NOEs cross-peaks were identified (see example in FIG. 12D) between Rhau18sm and T95_2 T. Using constraints from previously published data on T95_2 T (except restrained involving residues T1 and T2) intramolecular constraints of Rhau18sm and intermolecular, a model of Rhau18sm bound to T95_2 T was generated (FIG. 14). The top G-tetrad is almost entirely covered by the peptide. The appearance of such binding requires a high accessibility of said G-tetrad. In all non-parallel G-quadruplexes the top G-tetrad are not accessible and covered from the solvent by different types of loops, which may be the major structural determinant for the observed selectivity.

The invention has been described broadly and generically herein. Each of the narrower species and subgeneric groupings falling within the generic disclosure also form part of the invention. This includes the generic description of the invention with a proviso or negative limitation removing any subject-matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," containing", etc. shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The content of all documents and patent documents cited herein is incorporated by reference in their entirety.

The invention claimed is:

1. A conjugate comprising a peptide, wherein said peptide comprises or consists of (i) the amino acid sequence of SEQ ID NO:1 or (ii) an amino acid sequence having at least 80% sequence identity to the amino acid sequence of SEQ ID NO:1 over its entire length and further comprises at least one functional moiety, wherein said at least one functional moiety is conjugated to the N-terminus of said peptide with the proviso that said at least one functional moiety does not comprise the amino acid sequence set forth in SEQ ID NO:2 or a C-terminal fragment thereof.

2. The conjugate according to claim 1, with the proviso that said at least one functional moiety does not comprise the amino acid sequence set forth in SEQ ID NO:3 or an N-terminal fragment thereof.

3. The conjugate according to claim 1, wherein the functional moiety is a tag.

4. The conjugate according to claim 1, wherein the functional moiety is a pharmaceutically active compound.

5. A method for the detection of parallel-stranded G-quadruplexes in a sample wherein said method comprises:

contacting a sample suspected to contain a parallel-stranded G-quadruplex with the conjugate of claim 1; and detecting the presence or absence of the parallel-stranded G-quadruplex in said sample.

* * * * *

SEQUENCE LISTING

```
<160> NUMBER OF SEQ ID NOS: 32

<210> SEQ ID NO 1
<211> LENGTH: 16
<212> TYPE: PRT
<213> ORGANISM: Artificial Sequence
<220> FEATURE:
<223> OTHER INFORMATION: peptide of human Rhau protein

<400> SEQUENCE: 1

His Pro Gly His Leu Lys Gly Arg Glu Ile Gly Met Trp Tyr Ala Lys
```

```
<210> SEQ ID NO 2
<211> LENGTH: 52
<212> TYPE: PRT
<213> ORGANISM: Artificial Sequence
<220> FEATURE:
<223> OTHER INFORMATION: peptide of human Rhau protein

<400> SEQUENCE: 2

Met Ser Tyr Asp Tyr His Gln Asn Trp Gly Arg Asp Gly Gly Pro Arg
1               5                   10                  15

Ser Ser Gly Gly Gly Tyr Gly Gly Pro Ala Gly Gly His Gly Gly
            20                  25                  30

Asn Arg Gly Ser Gly Gly Gly Gly Gly Gly Gly Gly Arg Gly
        35                  40                  45

Gly Arg Gly Arg
    50

<210> SEQ ID NO 3
<211> LENGTH: 940
<212> TYPE: PRT
<213> ORGANISM: Artificial Sequence
<220> FEATURE:
<223> OTHER INFORMATION: peptide of human Rhau protein

<400> SEQUENCE: 3

Lys Gln Gly Gln Lys Asn Lys Glu Ala Glu Arg Gln Glu Arg Ala Val
1               5                   10                  15

Val His Met Asp Glu Arg Arg Glu Glu Ile Val Gln Leu Leu Asn
            20                  25                  30

Ser Val Gln Ala Lys Asn Asp Lys Glu Ser Glu Ala Gln Ile Ser Trp
            35                  40                  45

Phe Ala Pro Glu Asp His Gly Tyr Gly Thr Glu Val Ser Thr Lys Asn
        50                  55                  60

Thr Pro Cys Ser Glu Asn Lys Leu Asp Ile Gln Glu Lys Lys Leu Ile
65                  70                  75                  80

Asn Gln Glu Lys Lys Met Phe Arg Ile Arg Asn Arg Ser Tyr Ile Asp
                85                  90                  95

Arg Asp Ser Glu Tyr Leu Leu Gln Glu Asn Glu Pro Asp Gly Thr Leu
            100                 105                 110

Asp Gln Lys Leu Leu Glu Asp Leu Gln Lys Lys Lys Asn Asp Leu Arg
        115                 120                 125

Tyr Ile Glu Met Gln His Phe Arg Glu Lys Leu Pro Ser Tyr Gly Met
    130                 135                 140

Gln Lys Glu Leu Val Asn Leu Ile Asp Asn His Gln Val Thr Val Ile
145                 150                 155                 160

Ser Gly Glu Thr Gly Cys Gly Lys Thr Thr Gln Val Thr Gln Phe Ile
            165                 170                 175

Leu Asp Asn Tyr Ile Glu Arg Gly Lys Gly Ser Ala Cys Arg Ile Val
        180                 185                 190

Cys Thr Gln Pro Arg Arg Ile Ser Ala Ile Ser Val Ala Glu Arg Val
    195                 200                 205

Ala Ala Glu Arg Ala Glu Ser Cys Gly Ser Gly Asn Ser Thr Gly Tyr
    210                 215                 220

Gln Ile Arg Leu Gln Ser Arg Leu Pro Arg Lys Gln Gly Ser Ile Leu
225                 230                 235                 240
```

```
Tyr Cys Thr Thr Gly Ile Ile Leu Gln Trp Leu Gln Ser Asp Pro Tyr
                245                 250                 255
Leu Ser Ser Val Ser His Ile Val Leu Asp Glu Ile His Glu Arg Asn
            260                 265                 270
Leu Gln Ser Asp Val Leu Met Thr Val Val Lys Asp Leu Leu Asn Phe
        275                 280                 285
Arg Ser Asp Leu Lys Val Ile Leu Met Ser Ala Thr Leu Asn Ala Glu
290                 295                 300
Lys Phe Ser Glu Tyr Phe Gly Asn Cys Pro Met Ile His Ile Pro Gly
305                 310                 315                 320
Phe Thr Phe Pro Val Val Glu Tyr Leu Leu Glu Asp Val Ile Glu Lys
                325                 330                 335
Ile Arg Tyr Val Pro Glu Gln Lys Glu His Arg Ser Gln Phe Lys Arg
            340                 345                 350
Gly Phe Met Gln Gly His Val Asn Arg Gln Glu Lys Glu Glu Lys Glu
        355                 360                 365
Ala Ile Tyr Lys Glu Arg Trp Pro Asp Tyr Val Arg Glu Leu Arg Arg
370                 375                 380
Arg Tyr Ser Ala Ser Thr Val Asp Val Ile Glu Met Met Glu Asp Asp
385                 390                 395                 400
Lys Val Asp Leu Asn Leu Ile Val Ala Leu Ile Arg Tyr Ile Val Leu
                405                 410                 415
Glu Glu Glu Asp Gly Ala Ile Leu Val Phe Leu Pro Gly Trp Asp Asn
            420                 425                 430
Ile Ser Thr Leu His Asp Leu Leu Met Ser Gln Val Met Phe Lys Ser
        435                 440                 445
Asp Lys Phe Leu Ile Ile Pro Leu His Ser Leu Met Pro Thr Val Asn
450                 455                 460
Gln Thr Gln Val Phe Lys Arg Thr Pro Pro Gly Val Arg Lys Ile Val
465                 470                 475                 480
Ile Ala Thr Asn Ile Ala Glu Thr Ser Ile Thr Ile Asp Asp Val Val
                485                 490                 495
Tyr Val Ile Asp Gly Gly Lys Ile Lys Glu Thr His Phe Asp Thr Gln
            500                 505                 510
Asn Asn Ile Ser Thr Met Ser Ala Glu Trp Val Ser Lys Ala Asn Ala
        515                 520                 525
Lys Gln Arg Lys Gly Arg Ala Gly Arg Val Gln Pro Gly His Cys Tyr
530                 535                 540
His Leu Tyr Asn Gly Leu Arg Ala Ser Leu Leu Asp Asp Tyr Gln Leu
545                 550                 555                 560
Pro Glu Ile Leu Arg Thr Pro Leu Glu Glu Leu Cys Leu Gln Ile Lys
                565                 570                 575
Ile Leu Arg Leu Gly Gly Ile Ala Tyr Phe Leu Ser Arg Leu Met Asp
            580                 585                 590
Pro Pro Ser Asn Glu Ala Val Leu Leu Ser Ile Arg His Leu Met Glu
        595                 600                 605
Leu Asn Ala Leu Asp Lys Gln Glu Glu Leu Thr Pro Leu Gly Val His
610                 615                 620
Leu Ala Arg Leu Pro Val Glu Pro His Ile Gly Lys Met Ile Leu Phe
625                 630                 635                 640
Gly Ala Leu Phe Cys Cys Leu Asp Pro Val Leu Thr Ile Ala Ala Ser
                645                 650                 655
Leu Ser Phe Lys Asp Pro Phe Val Ile Pro Leu Gly Lys Glu Lys Ile
```

```
                    660                 665                 670
Ala Asp Ala Arg Arg Lys Glu Leu Ala Lys Asp Thr Arg Ser Asp His
                675                 680                 685

Leu Thr Val Val Asn Ala Phe Glu Gly Trp Glu Ala Arg Arg Arg
            690                 695                 700

Gly Phe Arg Tyr Glu Lys Asp Tyr Cys Trp Glu Tyr Phe Leu Ser Ser
705                 710                 715                 720

Asn Thr Leu Gln Met Leu His Asn Met Lys Gly Gln Phe Ala Glu His
                725                 730                 735

Leu Leu Gly Ala Gly Phe Val Ser Ser Arg Asn Pro Lys Asp Pro Glu
            740                 745                 750

Ser Asn Ile Asn Ser Asp Asn Glu Lys Ile Ile Lys Ala Val Ile Cys
            755                 760                 765

Ala Gly Leu Tyr Pro Lys Val Ala Lys Ile Arg Leu Asn Leu Gly Lys
            770                 775                 780

Lys Arg Lys Met Val Lys Val Tyr Thr Lys Thr Asp Gly Leu Val Ala
785                 790                 795                 800

Val His Pro Lys Ser Val Asn Val Glu Gln Thr Asp Phe His Tyr Asn
                805                 810                 815

Trp Leu Ile Tyr His Leu Lys Met Arg Thr Ser Ser Ile Tyr Leu Tyr
                820                 825                 830

Asp Cys Thr Glu Val Ser Pro Tyr Cys Leu Leu Phe Phe Gly Gly Asp
                835                 840                 845

Ile Ser Ile Gln Lys Asp Asn Asp Gln Glu Thr Ile Ala Val Asp Glu
            850                 855                 860

Trp Ile Val Phe Gln Ser Pro Ala Arg Ile Ala His Leu Val Lys Glu
865                 870                 875                 880

Leu Arg Lys Glu Leu Asp Ile Leu Leu Gln Lys Ile Glu Ser Pro
                885                 890                 895

His Pro Val Asp Trp Asn Asp Thr Lys Ser Arg Asp Cys Ala Val Leu
                900                 905                 910

Ser Ala Ile Ile Asp Leu Ile Lys Thr Gln Glu Lys Ala Thr Pro Arg
            915                 920                 925

Asn Phe Pro Pro Arg Phe Gln Asp Gly Tyr Tyr Ser
            930                 935                 940

<210> SEQ ID NO 4
<211> LENGTH: 18
<212> TYPE: RNA
<213> ORGANISM: Artificial Sequence
<220> FEATURE:
<223> OTHER INFORMATION: G-quadruplex forming RNA

<400> SEQUENCE: 4
ggguugcgga ggugggc                                                  18

<210> SEQ ID NO 5
<211> LENGTH: 12
<212> TYPE: RNA
<213> ORGANISM: Artificial Sequence
<220> FEATURE:
<223> OTHER INFORMATION: G-quadruplex forming RNA

<400> SEQUENCE: 5
uaggguuagg gu                                                       12

<210> SEQ ID NO 6
```

```
<211> LENGTH: 10
<212> TYPE: RNA
<213> ORGANISM: Artificial Sequence
<220> FEATURE:
<223> OTHER INFORMATION: G-quadruplex forming RNA

<400> SEQUENCE: 6
ggguuagggu                                                              10

<210> SEQ ID NO 7
<211> LENGTH: 18
<212> TYPE: DNA
<213> ORGANISM: Artificial Sequence
<220> FEATURE:
<223> OTHER INFORMATION: G-quadruplex forming DNA

<400> SEQUENCE: 7
ttgggtgggt gggtgggt                                                     18

<210> SEQ ID NO 8
<211> LENGTH: 21
<212> TYPE: DNA
<213> ORGANISM: Artificial Sequence
<220> FEATURE:
<223> OTHER INFORMATION: G-quadruplex forming DNA

<400> SEQUENCE: 8
tgagggtggt gagggtgggg a                                                 21

<210> SEQ ID NO 9
<211> LENGTH: 18
<212> TYPE: DNA
<213> ORGANISM: Artificial Sequence
<220> FEATURE:
<223> OTHER INFORMATION: G-quadruplex forming DNA

<400> SEQUENCE: 9
aggggggagg gagggtgg                                                     18

<210> SEQ ID NO 10
<211> LENGTH: 26
<212> TYPE: DNA
<213> ORGANISM: Artificial Sequence
<220> FEATURE:
<223> OTHER INFORMATION: G-quadruplex forming DNA

<400> SEQUENCE: 10
aagggtgggt gtaagtgtgg gtgggt                                            26

<210> SEQ ID NO 11
<211> LENGTH: 16
<212> TYPE: DNA
<213> ORGANISM: Artificial Sequence
<220> FEATURE:
<223> OTHER INFORMATION: G-quadruplex forming DNA

<400> SEQUENCE: 11
ggggtgggag gagggt                                                       16

<210> SEQ ID NO 12
<211> LENGTH: 24
<212> TYPE: DNA
<213> ORGANISM: Artificial Sequence
<220> FEATURE:
<223> OTHER INFORMATION: G-quadruplex forming DNA

<400> SEQUENCE: 12
```
ttgggttagg gttagggtta ggga                                    24

<210> SEQ ID NO 13
<211> LENGTH: 23
<212> TYPE: DNA
<213> ORGANISM: Artificial Sequence
<220> FEATURE:
<223> OTHER INFORMATION: G-quadruplex forming DNA

<400> SEQUENCE: 13
tagggttagg gttagggtta ggg                                     23

<210> SEQ ID NO 14
<211> LENGTH: 25
<212> TYPE: DNA
<213> ORGANISM: Artificial Sequence
<220> FEATURE:
<223> OTHER INFORMATION: G-quadruplex forming DNA

<400> SEQUENCE: 14
tagggttagg gttagggtta gggtt                                   25

<210> SEQ ID NO 15
<211> LENGTH: 22
<212> TYPE: DNA
<213> ORGANISM: Artificial Sequence
<220> FEATURE:
<223> OTHER INFORMATION: G-quadruplex forming DNA

<400> SEQUENCE: 15
gggttagggt tagggttagg gt                                      22

<210> SEQ ID NO 16
<211> LENGTH: 22
<212> TYPE: DNA
<213> ORGANISM: Artificial Sequence
<220> FEATURE:
<223> OTHER INFORMATION: G-quadruplex forming DNA

<400> SEQUENCE: 16
agggctaggg ctagggctag gg                                      22

<210> SEQ ID NO 17
<211> LENGTH: 12
<212> TYPE: DNA
<213> ORGANISM: Artificial Sequence
<220> FEATURE:
<223> OTHER INFORMATION: G-quadruplex forming DNA

<400> SEQUENCE: 17
cgcgaattcg cg                                                 12

<210> SEQ ID NO 18
<211> LENGTH: 52
<212> TYPE: DNA
<213> ORGANISM: Artificial Sequence
<220> FEATURE:
<223> OTHER INFORMATION: G-quadruplex forming DNA

<400> SEQUENCE: 18
acccacccac ccacccaaag atccgaaagg atctttgggt gggtgggtgg gt     52

<210> SEQ ID NO 19
<211> LENGTH: 55
<212> TYPE: PRT

<213> ORGANISM: Artificial Sequence
<220> FEATURE:
<223> OTHER INFORMATION: peptide of human Rhau protein

<400> SEQUENCE: 19

```
Ser Met His Pro Gly His Leu Lys Gly Arg Glu Ile Gly Met Trp Tyr
1               5                   10                  15

Ala Lys Lys Gln Gly Gln Lys Asn Lys Glu Ala Glu Arg Gln Glu Arg
            20                  25                  30

Ala Val Val His Met Asp Glu Arg Arg Glu Glu Gln Ile Val Gln Leu
        35                  40                  45

Leu Asn Ser Val Gln Ala Lys
    50                  55
```

<210> SEQ ID NO 20
<211> LENGTH: 29
<212> TYPE: PRT
<213> ORGANISM: Artificial Sequence
<220> FEATURE:
<223> OTHER INFORMATION: peptide of human Rhau protein

<400> SEQUENCE: 20

```
His Pro Gly His Leu Lys Gly Arg Glu Ile Gly Met Trp Tyr Ala Lys
1               5                   10                  15

Lys Gln Gly Gln Lys Asn Lys Glu Ala Glu Arg Gln Glu
            20                  25
```

<210> SEQ ID NO 21
<211> LENGTH: 23
<212> TYPE: PRT
<213> ORGANISM: Artificial Sequence
<220> FEATURE:
<223> OTHER INFORMATION: peptide of human Rhau protein

<400> SEQUENCE: 21

```
His Pro Gly His Leu Lys Gly Arg Glu Ile Gly Met Trp Tyr Ala Lys
1               5                   10                  15

Lys Gln Gly Gln Lys Asn Lys
            20
```

<210> SEQ ID NO 22
<211> LENGTH: 20
<212> TYPE: PRT
<213> ORGANISM: Artificial Sequence
<220> FEATURE:
<223> OTHER INFORMATION: peptide of human Rhau protein

<400> SEQUENCE: 22

```
His Pro Gly His Leu Lys Gly Arg Glu Ile Gly Met Trp Tyr Ala Lys
1               5                   10                  15

Lys Gln Gly Gln
            20
```

<210> SEQ ID NO 23
<211> LENGTH: 18
<212> TYPE: PRT
<213> ORGANISM: Artificial Sequence
<220> FEATURE:
<223> OTHER INFORMATION: peptide of human Rhau protein

<400> SEQUENCE: 23

```
His Pro Gly His Leu Lys Gly Arg Glu Ile Gly Met Trp Tyr Ala Lys
1               5                   10                  15
```

Lys Gln

<210> SEQ ID NO 24
<211> LENGTH: 20
<212> TYPE: PRT
<213> ORGANISM: Artificial Sequence
<220> FEATURE:
<223> OTHER INFORMATION: peptide of human Rhau protein

<400> SEQUENCE: 24

Ser Met His Pro Gly His Leu Lys Gly Arg Glu Ile Gly Met Trp Tyr
1               5                   10                  15

Ala Lys Lys Gln
            20

<210> SEQ ID NO 25
<211> LENGTH: 14
<212> TYPE: PRT
<213> ORGANISM: Artificial Sequence
<220> FEATURE:
<223> OTHER INFORMATION: peptide of human Rhau protein

<400> SEQUENCE: 25

His Pro Gly His Leu Lys Gly Arg Glu Ile Gly Met Trp Tyr
1               5                   10

<210> SEQ ID NO 26
<211> LENGTH: 12
<212> TYPE: PRT
<213> ORGANISM: Artificial Sequence
<220> FEATURE:
<223> OTHER INFORMATION: peptide of human Rhau protein

<400> SEQUENCE: 26

His Pro Gly His Leu Lys Gly Arg Glu Ile Gly Met
1               5                   10

<210> SEQ ID NO 27
<211> LENGTH: 5
<212> TYPE: PRT
<213> ORGANISM: Artificial Sequence
<220> FEATURE:
<223> OTHER INFORMATION: peptide of human Rhau protein

<400> SEQUENCE: 27

His Pro Gly His Leu
1               5

<210> SEQ ID NO 28
<211> LENGTH: 9
<212> TYPE: PRT
<213> ORGANISM: Artificial Sequence
<220> FEATURE:
<223> OTHER INFORMATION: peptide of human Rhau protein

<400> SEQUENCE: 28

Lys Gly Arg Glu Ile Gly Met Trp Tyr
1               5

<210> SEQ ID NO 29
<211> LENGTH: 15
<212> TYPE: PRT
<213> ORGANISM: Artificial Sequence
<220> FEATURE:
<223> OTHER INFORMATION: peptide of human Rhau protein

<400> SEQUENCE: 29

```
Lys Gly Arg Glu Ile Gly Met Trp Tyr Ala Lys Lys Gln Gly Gln
1               5                   10                  15

<210> SEQ ID NO 30
<211> LENGTH: 20
<212> TYPE: PRT
<213> ORGANISM: Artificial Sequence
<220> FEATURE:
<223> OTHER INFORMATION: peptide of human Rhau protein

<400> SEQUENCE: 30

His Pro Leu His Leu Lys Leu Arg Glu Ile Leu Met Trp Tyr Ala Lys
1               5                   10                  15

Lys Gln Gly Gln
            20

<210> SEQ ID NO 31
<211> LENGTH: 20
<212> TYPE: PRT
<213> ORGANISM: Artificial Sequence
<220> FEATURE:
<223> OTHER INFORMATION: peptide of human Rhau protein

<400> SEQUENCE: 31

His Pro Gly His Leu Lys Gly Arg Glu Ile Gly Met Ala Ala Ala Lys
1               5                   10                  15

Lys Gln Gly Gln
            20

<210> SEQ ID NO 32
<211> LENGTH: 13
<212> TYPE: PRT
<213> ORGANISM: Artificial Sequence
<220> FEATURE:
<223> OTHER INFORMATION: Highly conserved 13-amino-acid sequence
      identified as a major determinant for the G-quadruplex binding

<400> SEQUENCE: 32

Pro Gly His Leu Lys Gly Arg Glu Ile Gly Met Trp Tyr
1               5                   10
```